0
United States Patent [19]

Dunwell et al.

[11] 4,025,637

[45] May 24, 1977

[54] 2,5 OR 2,6 DISUBSTITUTED BENZOXAZOLES

[75] Inventors: David William Dunwell, Camberly; Delme Evans, Chalfont St. Peter; Terence Alan Hicks, Farnborough, all of England

[73] Assignee: Lilly Industries, Ltd., London, England

[22] Filed: Feb. 4, 1976

[21] Appl. No.: 655,668

Related U.S. Application Data

[63] Continuation-in-part of Ser. No. 515,133, Oct. 16, 1974, abandoned.

[30] Foreign Application Priority Data

Oct. 23, 1973 United Kingdom .............. 49260/73

[52] U.S. Cl. ........................... 424/272; 260/307 D; 260/299
[51] Int. Cl.$^2$ ....................... C07D 263/56
[58] Field of Search ...................... 260/307 D, 299; 424/272

[56] References Cited

OTHER PUBLICATIONS

Dunwell et al., C.A. 82, 118774b (1975), Abstract of J. Med. Chem. 1975, 18(1), pp. 53–58.

*Primary Examiner*—Raymond V. Rush
*Attorney, Agent, or Firm*—James L. Rowe; Everet F. Smith

[57] ABSTRACT

5- or 6-Substituted benzoxazole propionic or acetic acid derivatives, substituted in the 2-position of the oxazole nucleus by a group of the formula AR$^4$ wherein A is —CH$_2$—, —CO—, —CHOR—, or —NR—, wherein R is hydrogen, C$_{1-6}$ alkyl or C$_{2-7}$ acyl, and R$^4$ is optionally substituted phenyl, useful as non-steroidal, non-narcotic, analgesic, antipyretic and anti-inflammatory agents.

6 Claims, No Drawings

2,5 OR 2,6 DISUBSTITUTED BENZOXAZOLES

CROSS-REFERENCE

This application is a continuation-in-part of our copending application Ser. No. 515,133 filed Oct. 16th, 1974, now abandoned.

This invention relates to certain new benzoxazole derivatives which have been found to possess valuable pharmacological activity or are useful as intermediates for preparing such active compounds and to a process by which such compounds may be prepared. The invention also includes pharmaceutical compositions containing said pharmacologically active compounds and a method of treating animals including humans comprising administering thereto an effective dose of said compounds or compositions. The invention also provides novel intermediates from which the benzoxazole derivatives of the present invention may be prepared.

According to the present invention therefore, there are provided novel benzoxazole derivatives of the formula:

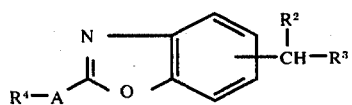
(I)

where the group

is in the 5- or 6-position of the benzoxazole nucleus, A is —CH$_2$—, —CO—,

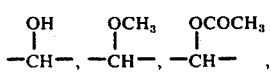

—NH— or —NCH$_3$—, R$^4$ is a phenyl group optionally substituted by one or two groups selected from halogen, trifluoromethyl, methyl, or methoxy, R$^2$ is hydrogen or methyl, and R$^3$ is the group COOR$^5$ wherein R$^5$ is C$_1$–C$_4$ alkyl or the group COOH or an alkali or alkaline earth metal, aluminum or ammonium salt thereof.

Examples of compounds falling within the scope of this invention are:

(i) 2-[2-benzyl-5-benzoxazolyl] acetic acid.
2-[2-benzyl-5-benzoxazolyl] propionic acid.
2-[2-(3,4-dimethylbenzyl)-6-benzoxazolyl] propionic acid.
2-[2-(4-methoxybenzyl)-6-benzoxazolyl[ propionic acid.
2-[2-(4-trifluoromethylbenzyl)-5-benzoxazolyl] acetic acid.
2-[2-(2,4-dichlorobenzyl)-6-benzoxazolyl] propionic acid.
2-[2-(4-chlorobenzyl)-5-benzoxazolyl] acetic acid.
2-[2-(4-chlorobenzyl)-5-benzoxazolyl]propionic acid.
2-[2-(4-bromobenzyl)-5-benzoxazolyl] propionic acid.
2-[2-benzoyl-5-benzoxazolyl]acetic acid.
2-[2-benzoyl-5-benzoxazolyl] propionic acid.
2-[2-(3,4-dimethylbenzoyl)-5-benzoxazolyl]propionic acid.
2-[2-(4-trifluoromethylbenzoyl)-5-benzoxazolyl] propionic acid.
2-[2-(2,4-dichlorobenzoyl)-5-benzoxazolyl] acetic acid.
2-[2-(α-hydroxybenzyl)-5-benzoxazolyl] acetic acid.
2-[2-(α-hydroxybenzyl)-5-benzoxazolyl]propionic acid.
2-[2-(α-hydroxy-4-chlorobenzyl)-5-benzoxazolyl]-propionic acid.
2-[2-(α-hydroxy-4-methoxybenzyl)-6-benzoxazolyl] propionic acid.
2-[2-(α-hydroxy-4-trifluoromethylbenzyl)-5-benzoxazolyl]propionic acid.
2-[2-(α-hydroxy-4-acetylbenzyl)-5-benzoxazolyl]-propionic acid.
2-[2-(α,4-dihydroxybenzyl)-6-benzoxazolyl]acetic acid.
2-[2-α-hydroxy-2,4-dichlorobenzyl)-5-benzoxazolyl]propionic acid.
2-[2-(α-hydroxy-4-bromobenzyl)-5-benzoxazolyl]-propionic acid.
2-[2-(α-methoxybenzyl)-5-benzoxazolyl]acetic acid.
2-[2-(α,4-dimethoxybenzyl)-6-benzoxazolyl]propionic acid.
2-[2-(α-acetoxy-4-β-chloroethylbenzyl)-5-benzoxazolyl]acetic acid.
2-[2-(α-acetoxy-4-trifluoromethylbenzyl)-5-benzoxazolyl]acetic acid.
2-[2-(α-acetoxy-2,4-dichlorobenzyl)-6-benzoxazolyl]propionic acid.
2-[2-(α-acetoxy-4-chlorobenzyl)-5-benzoxazolyl]acetic acid.
2-[2-(α-methoxy-4-chlorobenzyl)-5-benzoxazolyl]-propionic acid.
2-[2-(α-acetoxy-3,4-methylenedioxybenzyl)-5-benzoxazolyl]propionic acid.
2-[2-(α-methoxy-4-chlorobenzyl)-6-benzoxazolyl] propionic acid.
2-[2-anilino-5-benzoxazolyl]propionic acid.
2-[2-(N-methylanilino)-5-benzoxazolyl]propionic acid.
2-[2-(N,3,4-trimethylanilino)-5-benzoxazolyl]propionic acid.
2-[2-(4-methoxyanilino)-5-benzoxazolyl]propionic acid.
2-[2-(4-trifluoromethylanilino)-6-benzoxazolyl]acetic acid.
2-[2-(2,4-dichloroanilino)-6-benzoxazolyl]propionic acid.
2-[2-(N-methyl-4-bromoanilino)-5-benzoxazolyl]acetic acid.
2-[2-anilino-6-benzoxazolyl]acetic acid.
2-[2-(4-chloroanilino)-5-benzoxazolyl]propionic acid.
2-[2-anilino-6-benzoxazolyl]propionic acid.

(ii) the sodium, potassium, calcium, aluminum and ammonium salts of the acids described at (i) above; and (iii) the C$_{1-4}$ alkyl, especially the methyl and ethyl, esters of the acids described at (i) above.

The present invention also provides a process for the preparation of the foregoing compounds of formula (I), which process comprises cyclising a compound of the formula:

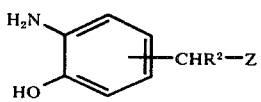

(II)

wherein Z is the group $R^3$ or is a group convertible to $R^3$, using a cyclising agent capable of donating the required group $R^4$—A— or another group which is convertible to $R^4$—A—, and thereafter where necessary the resultant compound is converted to the desired compound of formula (I) in conventional manner.

In the case where A in the end-product of formula (I) is —$CH_2$— or —CHOR where R is hydrogen or methyl, the compound of formula (I) may be obtained directly by reacting an appropriate cyclising agent such as a compound of the formula $R^4$—A—COOH, ($R^4$—A—CO)$_2$O, $R^4$—A—COCl, $R^4$—A—$CONH_2$, $R^4$—A—$CONHNH_2$ or $R^4$—A—CN, with the compound of formula (II), the reaction being carried out under the influence of heat and/or under acidic conditions, for example in the presence of hydrochloric acid, phosphorus oxychloride or polyphosphoric acid, or under basic conditions, for example in the presence of pyridine or triethylamine depending on the particular reactants involved.

It is believed that the above cyclisation proceeds via an intermediate in which one or more of the hydrogen atoms in the amino or phenolic groups have been replaced by a radical from the cyclising agent. For example, when the cyclising agent is a compound of formula $R^4$—A—COOH, $R^4$—A—COCl, $R^4$—A—$CONH_2$, $R^4$—A—$CONHNH_2$ or $R^4$—A—CHO, the hydrogen atom in the phenolic hydroxyl group can be replaced by a $R^4$—A—CO—group and one or both of the hydrogen atoms in the amino group can be replaced by $R^4$—A—CO— as before or by the group $R^4$—A—CH= (when the aldehyde is used as cyclising agent). When A is —$CH_2$—, the intermediates are stable and can, if desired, be isolated prior to ring closure to the benzoxazole.

In the case where the cyclising agent is $R^4$—A—CHO, the ring closure can be carried out in the presence of an oxidising agent such as lead tetra-acetate or nickel peroxide.

In the case where A in the end-product of formula I is —CO— or —CHOR— where R is acetyl, the desired compound may be obtained from the corresponding compound, prepared as described above, in which A is —CHOH— by oxidation, for example using manganese dioxide or chromium trioxide, or by conventional acylation respectively.

In the case where A in the end-product of formula I is —NH— the intermediate of formula(II) can be ring-closed with an isocyanate of formula $R^4$CNO to yield directly the compound of formula I. Alternatively, the intermediate of formula(II) can be cyclised to a benzoxazolyl-2-thione, for example by using an alkali metal alkyl xanthate such as potassium ethyl xanthate as the cyclising agent, and the thione can then be converted to the corresponding 2-halo compound, for example 2-chlorobenzoxazole, by halogenation for example with chlorine gas. To obtain the compound of formula(I) in which A is —NR—, wherein R is methyl, the 2-halocompound is then reacted with the appropriate aniline of formula $R^4$—NHR. Alternatively, the thione can be reacted directly with the aniline.

Those benzoxazole 2-thiones and halides in which $R^3$ is a nitrile, carboxylic acid or salt, amido, ester or hydroxamic acid group, are novel compounds. Writing the thione group in its thiol form, these compounds can be represented by the formula:

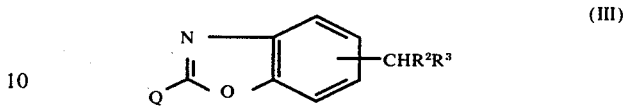

(III)

where Q is SH or halogen.

As will immediately be apparent to those skilled in the art, intermediates of formula IV in which Q is a halogen atom, for example iodine, can also be converted to 2-phenyl derivatives using, for example, the well-known Ullmann reaction (see for instance page 1222-The Merck Index, VIII the edition published 1968). The reactants and reaction conditions necessary for this reaction will be well known to those skilled in the art, however, for illustrative purposes the following reaction scheme may be considered typical:

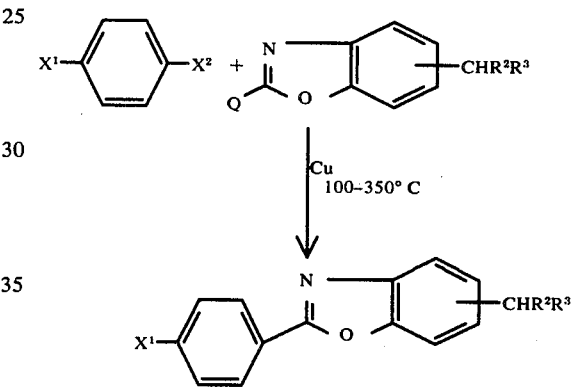

wherein $X^1$ is hydrogen or halogen, and wherein Q and $X^2$ are also halogen.

In carrying out the foregoing reactions, it will be appreciated that, if group Z in the starting material of formula (II) is capable of reacting with the cyclising agent or other reactants used, the reaction may produce a mixture of products rather than the desired compound of formula I alone. Although the undesired products could be separated from the reaction mixture, it is obviously desirable to use a compound of formula(II) in which Z is a group which is incapable of reaction with the other reactants. Thus where Z is a group convertible to $R^3$, Z is preferably hydrogen or halogen and where Z is one of the groups encompassed by $R^3$, it is preferably a nitrile group or an esterified carboxy, salified carboxy or carboxyamide group.

As stated above, when Z is not the group $R^3$, completion of the cyclisation step must be followed by conversion of group Z to the desired group $R^3$. As is well known in the art, many different types of groups may be converted to the $R^3$ functions in the desired compounds of this invention. However, it is preferred for the purposes of the present invention that, where Z is not the group $R^3$, it is hydrogen or halogen. When Z is hydrogen, the compound resulting from the cyclisation reaction may be halogenated in conventional manner, for example using chlorine, sulphurylchloride, bromine or N-bromosuccinimide, preferably in the presence of a suitable solvent such as carbon tetrachloride to produce the corresponding compound in which Z is halogen. This compound, or the same compound obtained from the above cyclisation reaction, may then be reacted with an alkali metal cyanide in a suitable diluent or solvent, usually under the influence of heat, to produce a compound in which Z is CN. The latter compound, or the same compound obtained directly from the above cyclisation reaction, may then be treated in a number of ways to achieve its conversion to a compound of formula (I). For example, the nitrile may be reacted with an appropriate alcohol under acidic conditions to produce a compound of formula (I) in which $R^3$ is an esterified carboxy group. Alternatively, the nitrile can be hydrolysed, for example using sulphuric acid, to produce a carboxyamide compound. Hydrolysis of the nitrile, or the last mentioned carboxyamide, with a strong base or an acid such as concentrated hydrochloric acid results in the formation of a compound of formula (I) in which $R^3$ is a carboxy group.

In addition, a resultant compound of formula II in which Z is a halogen can be converted to the corresponding acid using the well-known Grignard reaction (see for example page 1172 of the Merck Index, VIIIth Edition published 1968 or any other standard reference text). After reaction with Magnesium and treatment with $CO_2$, a compound of formula I is formed in which $R^3$ is the group

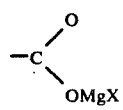

where X is a halogen atom. This group can then be converted to a carboxylic acid group simply by hydrolysis.

An acid of formula I may be salified by treatment with an appropriate base such as an ammonium, alkylammonium, aralkylammonium, aluminum, alkali metal or alkaline earth metal hydroxide and of course a salt of formula I may readily be converted to the free acid by treatment with an acid such as hydrochloric or sulphuric acid. An acid of formula I or a salt thereof may be converted to an ester by treatment with an appropriate alcohol or by treatment with a halide of the appropriate ester moiety or a salt of that halide if the ester moiety contains a basic nitrogen atom. An ester of formula I may of course by hydrolysed to the corresponding acid of formula I by treatment with a suitable hydrolytic agent such as an inorganic base or acid. An acid of formula I or an ester thereof may also be converted to an amide of formula I by reaction with ammonia or an appropriate primary or secondary amine.

A resultant compound of formula (I) in which $R^2$ is hydrogen may be alkylated to produce the corresponding compound of formula (I) in which $R^2$ is methyl. The alkylation may be carried out by interaction of an alkali metal derivative of the appropriate benzoxazole derivative with an alkyl halide such as, for example, methyl iodide.

The compounds of formula (I) can be prepared by a process which comprises the hydrolysis of a compound of formula (IV):

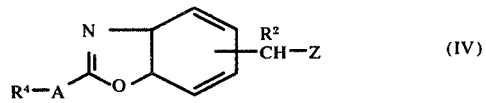

where Z represents a nitrile, ester, carboxylate, amido, hydroxamic acid group, or a group of formula :

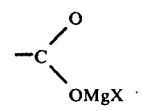

where X is a halogen atom

The compounds of formula (II) above may be prepared by reducing the corresponding nitro compounds, which may themselves be readily obtained from known or easily prepared chemicals according to the following reaction scheme:

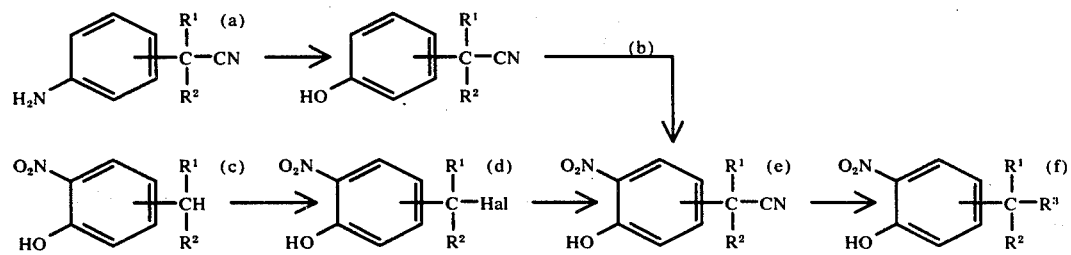

In the above scheme, step (a) is accomplished by diazotization followed by treatment of the resultant diazonium salt with dilute sulphuric acid. Step (b) is carried out by nitration, for example by addition of nitric acid to a solution of the nitrile in glacial acetic acid. Steps (c), (d) and (e) are as described above in connection with the conversion of Z=H → Z=Halogen → Z=CN → Z=$R^3$.

The compounds of formula I above in which $R^3$ is a nitrile group are, as can be seen from the foregoing description, useful as intermediates for conversion to other compounds of formula I. The other compounds of formula I are useful in that they are pharmacologically active. In particular, they have been shown to have low toxicity and to possess an aspirin-like pharmaceutical action, i.e. they possess analgesic, antipyretic and anti-inflammatory activity. However, in the treatment of mammals with the compounds of this invention one, two or three of the above conditions may be present in the suffering mammal, which condition or conditions are alleviated by out novel treatment method.

The foregoing activities have been demonstrated in tests carried out in animals usually at doses of from 0.1 to 250 mg kg. In the treatment of humans, the dose administered may be, for example, between 0.1 and 25 mg/kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, satchet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene, sorbitan monolaurate, methyl- or propyl-hydroxybenzoate, ethyl cellulose acetate phthalate, low viscosity acetyl cellulose acetate, paraffin wax, mineral wax, vegetable wax, vegetable gum, silicone rubbers such as liquid polydimethyl-siloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg. (preferably 25 to 500 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicylic acid and salts thereof, caffeine, codeine phosphate, phenylbutazone, paracetamol, dextropropoxyphene and indomethacine.

The compositions of the present invention will, of course be adapted to the particular route of administration. Thus, for oral administration, tablets, pills, capsules, solutions or suspensions may be used; for parenteral administration, sterile injection solutions or suspensions may be used; for rectal administration, suppositories may be used; and for topical administration, creams, lotions or ointments may be used. Any of the foregoing compositions may, of course, be formulated in delayed or sustained release form in manner well known in the art.

The following examples will further illustrate the preparation of the compounds of formula I.

EXAMPLE 1 a. Phenyl acetyl chloride (2.2 ml.) was added to a stirred solution of ethyl 2-(3-amino-4-hydroxyphenyl)-propionate(3.15g.) in anhydrous pyridine (50 ml.) and the solution was heated at 100° C for two hours. Excess pyridine was removed by distillation and the residue heated until the temperature of the distillate immediately above the reaction mixture was 200° C. The resultant dark brown gum was dissolved in ether (75 ml.) and then washed with water (3 × 50 ml.) The ether solution was extracted with 1N sodium hydroxide (50 ml.), washed with water (2 × 50 ml.) and evaporated to give ethyl 2-(2-benzyl-5-benzoxazolyl) propionate as a light brown mobile gum, which was shown to be pure by thin layer chromatography. Similarly the following esters were prepared and characterised:

(b) Ethyl 2-[2-(4-chlorobenzyl)-5-benzoxazolyl] acetate (c) Ethyl 2-[2-(4-chlorobenzyl)-6-benzoxazolyl] acetate (d) Ethyl 2-[2-(4-chlorobenzyl)-6-benzoxazolyl] propionate (e) Ethyl 2-[2-benzyl-6-benzoxazolyl] acetate (f) Ethyl 2-[2-(3,4-dichlorobenzyl)-5-benzoxazolyl] propionate g. 4-Chlorophenyl acetyl chloride (5.5g.) was added dropwise to a solution of ethyl 2-(3-amino-4-hydroxyphenyl)propionate (5.5g.) in pyridine (20ml.). The solution was heated on a steam bath for 2 hours. Excess pyridine was removed by distillation and the residue heated until the temperature of the distillate immediately above the reaction mixture was 230° C. The resultant dark brown gum was dissolved in chloroform. The chloroform solution was washed with 2N-sodium hydroxide, water, 2N-hydrochloric acid and water. The chloroform solution was then stirred with charcoal and anhydrous sodium sulphate, filtered and evaporated to give ethyl 2-[2-(4-chlorobenzyl)-5-benzoxazolyl] propionate as a brown gum.

EXAMPLE 2 a. 2N-sodium hydroxide (15 ml.) was added to ethyl 2-[2-benzyl-5-benzoxazolyl] propionate (3.1 g.) in ethanol (20 ml.). After two hours at room temperature, water (50 ml.) was added and the volume reduced to a quarter by evaporation at 40° C. The resulting cooled solution was extracted with ether (2 × 25 ml.). acidified with concentrated hydrochloric acid and again extracted with ether (3 × 50 ml.) The ether extracts were washed with water (2 × 25 ml.), dried over sodium sulphate and evaporated. The residue was crystallised from acetone to yield 2-[2-benzyl-5-benzoxazolyl] propionic acid, m.p 136° –8° C.

Similarly the following acids were prepared (the structures of the acids being confirmed by microanalysis):

(b) 2-[2-(4-chlorobenzyl)-5-benzoxazolyl]acetic acid (c) 2-[2-(4-chlorobenzyl)-6-benzoxazolyl]acetic acid.

(d) 2-[2-(4-chlorobenzyl)-6-benzoxazolyl]propionic acid (e) 2-[2-benzyl-6-benzoxazolyl]acetic acid (f) 2-[2-(3,4-dichlorobenzyl)-5-benzoxazolyl]propionic acid.

g. 2N-Sodium hydroxide solution (30 ml.) was added to the ethyl ester (5.8 g.) prepared in Example 1(g) in ethanol (40 ml). After 2 hours stirring at room temperature the volume was reduced by evaporation at 40° C and the solution diluted with water (120 ml.). It was then extracted with ether (x2) acidified with concentrated hydrochloric acid and then extracted with chloroform (x3). The combined chloroform extracts were washed with water, dried over anhydrous sodium sulphate and evaporated to give an oil. This oil was purified using prep. tlc plates to give 2-[2-(4-chlorobenzyl)-5-benzoxazolyl]propionic acid, m.p. 135°–7° C, which was characterised by IR, UV and NMR spectroscopy and by micro analysis which gave C 64.41%, H 4.71%, N 4.57%, $C_{17}H_{14}$; Cl $NO_3$ requires C64.66%, H 4.44%, N 4.44% h. A mixture of ethyl 3-amino-4-hydroxy-phenyl-propionate(4 g.), 4-fluoro-phenyl-acetic acid (3 g.), p-toluene sulphonic acid (0.1 g.) and xylene (50 ml.) was heated under reflux for 20 hours and the water wich formed was removed using a Dean and Stark apparatus. The solution was evaporated to dryness and the residue dissolved in ether. The solution was washed with 2N-sodium hydroxide solution (x2) and water, then stirred with charcoal and anhydrous sodium sulphate, filtered and evaporated to dryness. The residual oil (3.7 g., $N_D^{22.5}$ 1.5469) was dissolved in ethanol (30 ml.) and 2N-sodium hydroxide solution (30 ml) was added with stirring over 15 minutes. The reaction mixture was stirred for 2½ hours during which time water (250 ml) was slowly added. The solution was extracted with ether (x2), acidified with concentrated hydrochloric acid and then extracted with ether (x3). These ethereal extracts were washed with water, dried over anhydrous sodium sulphate and evaporated to give an oil. This oil was purified using prep. tlc plates to give 2-[2-(4-fluorobenzyl)-5-benzoxazolyl]propionic acid as a white solid, mpt 91°–93° C, which was characterised by IR UV and NMR spectroscopy and by microanalysis which gave C 68.40%, H 3.86%, N4.64%; $C_{17}H_{14}FNO_3$ requires C68.23%, H 4.68%, N 4.68% i. 2, 6-Dichloro-phenyl-acetic acid (15.1 g.) was added portionwise with warming to thionyl chloride (30 ml.). The solution was heated on a steam bath for half an hour then allowed to stand at room temperature for 2½ hours. The excess of thionyl chloride was removed by distillation under reduced pressure and the residue was distilled to give the acid chloride as a colourless oil, bpt 149°–150°/15 mm.

This oil (14.8g) was added in small portions to a solution of ethyl 3-amino-4-hydroxy-phenyl-propionate (13 g.) in pyridine (30 ml.) The resulting solution was heated on a steam bath for 2 hours. Excess pyridine was removed by distillation and the residue heated until the temperature of the distillate immediately above the reaction mixture was 210° C. After 5 minutes the reaction mixture was allowed to cool and was then dissolved in ether. The ethereal solution was washed with 2N-sodium hydroxide solution (x2) and water, dried over anhydrous sodium sulphate and evaporated to dryness. The residue was triturated with a small amount of ether to give a white solid (1.6g) which was removed by filteration (the ir spectrum of the solid suggested that it was uncyclised material). The ethereal solution was evaporated to give an oil.

This oil (11 g.) was dissolved in ethanol (40 ml.) and 2N-sodium hydroxide solution (40 ml.) was added in portions during 15 minutes. The reaction was stirred at room temperature for 2 hours and was then diluted with water (400 ml.). The solution was extracted with ether (x2), acidified with concentrated hydrochloric acid and then extracted with ether (x3). These last ethereal extracts were washed with water, dried over anhydrous sodium sulphate and evaporated to give an oil. This oil was purified using prep. tlc plates to give 2-[2-(2,6-dichlorobenzyl)-5-benzoxazolyl] propionic acid as a white solid, mpt 122°–124° C, which was characterised by IR, UV and NMR spectroscopy and by microanalysis which gave C58.58%, H3.78%, N3.90%; $C_{17}H_{13}Cl_2NO_3$ requires C58.29%, H3.71%, N4.00% j. The compound 2-[2-(2-chlorobenzyl)-5-benzoxazoyl] propionic acid was prepared in an exactly analogous manner to the procedure adopted in Example 2(h). The product was isolated as a white powder, m.p. 92°–4° C.

EXAMPLE 3 a. A mixture of 2-(3-amino-4-hydroxyphenyl)propionitrile (4.86 g.), potassium ethylxanthate (5.3 g.), ethanol (30 ml.) and water (5.0 ml.) was heated under reflux for four hours. The mixture was filtered, diluted with water (15 ml.), acidified with acetic acid and then diluted with more water. The resulting brown precipitate was filtered off and recrystallised from aqueous ethanol to give 2-(2-thioxo-2,3-dihydrobenzoxazol-5-yl) propionitrile, m.p. 173°–6° C. Dry chlorine was passed into a suspension of the thione (8.0 g.) in freshly dried and distilled chloroform (200 ml.). After 20 hours, most of the solid had dissolved and the mixture was filtered. The filtrate was washed with water (100 ml.), 1N sodium hydroxide (50 ml.) and water (3 × 100 ml.) The dried ($Na_2SO_4$) organic solution was evaporated to yield 2-[2-chloro-5-benzoxazolyl]propionitrile as a brown oil which was shown to be a single compound by thin layer chromatography. The oil distilled at 128°–134° C/0.3 mm.Hg.

A mixture of the 2-chloro compound (6.15 g.) and p-chloroaniline (10.0 g.) was heated at 100° C for 3½ hours. The residue was equilibrated between chloroform (100 ml.) and 2N hydrochloric acid (100 ml.). The chloroform layer was washed with water (2 × 100 ml.), 1N sodium hydroxide (100 ml.) and water (3 × 100 ml.). Evaporation of the dried ($Na_2SO_4$) solution gave 2-[2-(4-chloroanilino)-5-benzoxazolyl]propionitrile as a cream solid which was characterised by n.m.r. spectroscopy.

Similarly, the following nitriles were prepared and characterised:-

(b) 2-[2-anilino-5-benzoxazolyl]propionitrile (c) 2-[2-(N-methylanilino)-5-benzoxazolyl]propionitrile (d) 2-[2-(N,4-dimethylanilino)-6-benzoxazolyl]acetonitrile (e) 2-[2-(4-chloroanilino)-6-benzoxazolyl]acetonitrile (f) 2-[2-(4-chloroanilino)-5-benzoxazolyl)acetonitrile (g) 2-[2-(N-methyl-3,4-dichloroanilino)-5-benzoxazolyl]propionitrile (h) 2-[2-(4-methoxyanilino)-6-benzoxazolyl]propionitrile i. A stirred mixture of ethyl 2-(3-amino-4-hydroxyphenyl)propionate (8.4 g.), potassium ethylxanthate (6.33 g.), ethanol (38 ml.) and water (6.5 ml.) was heated under reflux for 4 hours. The solution was evaporated to half volume and diluted with water (65 ml.). The mixture was acidified with 2N-hydrochloric acid and extracted several times with ether. The ethereal solution was washed with water, then dried with anhydrous sodium sulphate, and evaporated to give ethyl 2-(2-thioxo-2,3-dihydrobenzoxazol-5-yl)propionate as an oil. Dry chlorine was passed into a solution of the thione (9 g.) in freshly dried and distilled chloroform (150 ml.) with stirring for 4 hours. The solution was then washed with water, N-sodium hydroxide solution, then water (3x). The dried ($Na_2SO_4$) organic solution was evaporated to yield ethyl 2-(2-chloro-5-benzoxazolyl)propionate as a brown oil which was shown to be a single compound by thin layer chromatography.

j. A mixture of the 2-chloro compound (12.5 g.) of Example 3(i) and p-chloroaniline (25 g.) was heated on a steam bath for one hour. The reaction mixture was dissolved in chloroform and the solution was washed with 2N hydrochloric acid (2x), water, 2N sodium hydroxide solution (2x) and water (3x). The chloroform solution was stirred with charcoal and anhydrous sodium sulphate, then filtered and evaporated. The residue was purified using prep t.l.c. plates to give ethyl-2-[2-(4-chloroanilino)-5-benzoxazolyl]propionate, mpt 135°–7° C, which was characterised by ir uv and nmr spectroscopy and by micro analysis which gave C62.45%, H5.11%, N7.97% $C_{18}H_{17}ClN_3O_2$ requires C62.70%, H4.93%, N8.13%

EXAMPLE 4 a. 2-[2-(4-chloroanilino)-5-benzoxazolyl]propionitrile (2.75 g.) and concentrated hydrochloric acid (20 ml.) were heated together under reflux for 2½ hours. The cooled mixture was neutralised to pH5 with 5N sodium hydroxide and the resultant solid filtered off, washed with a small amount of ice-water and dried. The solid was partitioned between 0.1 N sodium hydroxide and chloroform. The aqueous layer was washed several times with chloroform, adjusted to pH3 and the product extracted with chloroform. The chloroform extract was then washed with water, dried over sodium sulphate and evaporated to yield 2-[2-(4-chloroanilino)-5-benzoxazolyl]propionic acid, which was shown to be pure by thin layer chromatography (m.p. 206°–8° C.).

Similarly the following acids were prepared:
(b) 2-[2-anilino-5-benzoxazolyl]propionic acid
(c) 2-[2-(N-methylanilino)-5-benzoxazolyl)propionic acid
(d) 2-[2-(N,4-dimethylanilino)-6-benzoxazolyl]acetic acid
(e) 2-[2-(4-chloroanilino)-6-benzoxazolyl]acetic acid
(f) 2-[2-(4-chloroanilino)-5-benzoxazolyl]acetic acid
(g) 2-[2-(N-methyl-3,4-dichloroanilino)-5-benzoxazolyl]propionic acid
(h) 2-[2-(4-methoxyanilino)-6benzoxazolyl]propionic acid. Production of the acids was confirmed by thin-layer chromatography.

i. A stirred mixture of ethyl 2-[2-(4-chloroanilino)-5-benzoxazolyl] propionate (2.9g.), dry lithium iodide (10g.), sodium cyanide (0.4g.) and methyl ethyl ketone (35 ml.) was heated under reflux for 18 hours. The solution was diluted with water and made alkaline with sodium bicarbonate. The solution was washed several times with chloroform, filtered through a Supercel pad and acidified with concentrated hydrochloric acid. The solid obtained was filtered off, washed with water and recrystallised from aqueous methanol to give 2-[2-(4-chloroanilino)-5-benzoxazolyl] propionic acid as a buff powder, mpt 206°–8° C, which was characterised by ir, uv and NMR spectroscopy and by micro analysis which gave: C60.45%, H4.31%, N8.75%.; $C_{16}H_{13}ClN_2O_3$ requires C60.66%, H4.11%, N 8.85%

EXAMPLE 5 a. A mixture of ethyl 2-(3-amino-4-hydroxyphenyl)-propionate (1.2 g.), mandelic acid (1 g.) and xylene (50 ml.) was heated using a Dean and Stark apparatus. After 24 hours, the solution was evaporated to dryness and the residue was taken up in chloroform. This solution was washed first with sodium hydroxide solution, then with hydrochloric acid and finally dried over sodium carbonate. The solution was evaporated to dryness to give ethyl 2[2-(α-hydroxybenzyl)-5-benzoxazolyl]propionate, the structure of which was confirmed by n.m.r. spectroscopy.

Similarly the following esters were prepared and characterised:
(b) ethyl 2-[2-(α-methoxybenzyl)-5-benzoxazolyl]-propionate.
(c) ethyl 2-[2-(α-hydroxy-3,4-dichlorobenzyl)-6-benzoxazolyl] acetate
(d) ethyl 2-[2-(α-hydroxy-4-chlorobenzyl)-6benzoxazolyl]propionate.
(e) ethyl 2-[2-(α-hydroxybenzyl)-5-benzoxazolyl]acetate f. A mixture of ethyl 3-amino-4-hydroxyphenyl propionate (10 g.), 4-chloromandelic acid (9.33 g.) and xylene (150 ml.) was heated under reflux for 22 hours and the water which formed was removed using a Dean and Stark apparatus. The solution was evaporated to dryness and the residue dissolved in ether. The solution was washed with NaOH, HCl and water, then stirred with charcoal and anhydrous sodium sulphate, filtered and evaporated to dryness. The residual oil (15 g.) was dissolved in a small amount of chloroform and chromatographed on a silicar gel column using chloroform as eluting solvent; the first fractions containing a carbonyl compound being discarded. The crude product obtained was purified using silicar prep. tlc plates to give ethyl 2-[2-(α-hydroxy-4-clorobenzyl)-5-benzoxazolyl]propionate as a gum, $N_D^{21.4}$ 1.5681. The structure was confirmed by IR, UV and NMR spectroscopy and by microanalysis which gave C62.54%, H5.20%, N3.79%; $C_{19}H_{18}ClNO_4$ requires C63.4%, H5.01%, N3.89%.

EXAMPLE 6 a. A mixture of 3-amino-4-hydroxyhydratroponitrile (10 g.), mandelic acid (14 g.) and xylene (300 ml.) was heated using a Dean and Stark apparatus for 24 hours. The solution was filtered, evaporated to dryness and the residue dissolved in chloroform. The solution was washed with acid and base, dried over sodium carbonate and was eluted down a silica gel column with ether to give 2-[2-(α-hydroxybenzyl)-5-benzoxazolyl] propionitrile, the structure of which was confirmed by n.m.r. spectroscopy.

Similarly the following nitriles were prepared and characterised:
(b) 2-[2-(α-methoxybenzyl)-5-benzoxazolyl]propionitrile.
(c) 2-[2-(α-hydroxy-4-chlorobenzyl)-5-benzoxazolyl]propionitrile.
(d) 2-[2-(α-hydroxy-3,4-dichlorobenzyl)-6-benzoxazolyl]acetonitrile.
(e) 2-[2-(α-hydroxy-4-chlorobenzyl)-6-benzoxazolyl]propionitrile.
(f) 2-[2-)α-hydroxybenzyl)-5-benzoxazolyl]acetonitrile.

EXAMPLE 7

By hydrolysis of the esters of Example 5 using the method of Example 2 or by hydrolysis of the nitriles of Example 6 using the method of Example 4, the following acids were obtained:
 (a) 2-[2-(α-hydroxybenzyl)-5-benzoxazolyl]propionic acid
 (b) 2-[2-(α-methoxybenzyl)-5-benzoxazolyl]propionic acid
 (c) 2-[2-(α-hydroxy-3,4-dichlorobenzyl)-6-benzoxazolyl]acetic acid
 (d) 2-[2-(α-hydroxy-4-chlorobenzyl)-5-benzoxazolyl]propionic acid.
 (e) 2-[2-(α-hydroxy-4-chlorobenzyl)-6-benzoxazolyl]propionic acid
 (f) 2-[2-(α-hydroxybenzyl)-5-benzoxazolyl]acetic acid.

Microanalysis carried out on the above acids was in full accord with the expected structures.

EXAMPLE 8 a. A solution of ethyl 2-[2-(α-hydroxy-4-chlorobenzyl-5-benzoxazolyl]propionate (5 g.) in glacial acetic acid (25 ml.) was slowly added to a stirred solution of chromium trioxide (1.4 g.) in glacial acetic acid (75 ml). The temperature of the reaction mixture was slowly raised to 115° C. and maintained at this temperature for 30 minutes. The solution was evaporated to a small bulk and the residue diluted with water and extracted with chloroform. The chloroform solution was dried over anhydrous sodium sulphate and evaporated to give an oil which was partially purified using prep tlc plates. The oil thus obtained was triturated with 40–60 petroleum ether to give ethyl 2-[2-(4-chlorobenzolyl)-5-benzoxazolyl]propionate as a white solid, m.p. 66°–7° C. The structure was confirmed by IR, UV and NMR spectroscopy and by microanalysis which gave C64.01%, H4.64%, N4.11%; $C_{19}H_{16}ClNO_4$ requires C63.78%, H4.48%, N3.92%.

Similarly, on oxidation of the α-hydroxybenzyl compounds of Example 7, the following other benzoyl compounds were obtained:
 (b) 2-[2-benzoyl-5-benzoxazolyl]propionic acid
 (c) 2-[2-(3,4-dichlorobenzloyl)-6-benzoxazolyl]acetic acid
 (d) 2-[2-(4-chlorobenzoyl)-5-benzoxazolyl]propionic acid
 (e) 2-[2-(4-chlorobenzolyl)-6-benzoxazolyl]propionic acid
 (f) 2-[2-benzolyl-5-benzoxazolyl]acetic acid g. The benzoyl compounds of Examples 8(b) to (f) were also prepared from the α-hydroxybenzyl compounds of Example 7 using manganese dioxide as the oxidising agent. The compounds of Examples (b) to (g) were characterised by thin layer chromatography.

EXAMPLE 9

On acylation of the α-hydroxybenzyl compounds of Example 7 using acetyl chloride, the acylation being carried out in the presence of sodium bicarbonate and in toluene as solvent, the following α-acetoxybenzyl compounds were obtained:
 (a) 2-[2-)α-acetoxybenzyl)-5-benzoxazolyl]propionic acid
 (b) 2-[2-(α-acetoxy-3,4-dichlorobenzyl)-6-benzoxazolyl] acetic acid
 (c) 2-[2-(α-acetoxy-4-chlorobenzyl)-5-benzoxazolyl] propionic acid.
 (d) 2-[2-(α-acetoxy-4-chlorobenzyl)-6-benzoxazolyl] propionic acid
 (e) 2-[2-(α-acetoxybenzyl)-5-benzoxazolyl] acetic acid.

Microanalysis for the above compounds was in accord with their expected structures.

EXAMPLE 10 a. Phenyl acetyl chloride (28.0 g.) was added over 20 minutes to a cooled stirred solution of 2(3-amino-4-hydroxyphenyl) propionitrile (29.0 g.) in anhydrous pyridine (200 ml.) at 0°–3° C. After addition was complete, the mixture was heated at 100° C. for 1 hour. After evaporation under reduced pressure, 2-(3-phenylacetamido-4-hydroxyphenyl)propionitrile was isolated as an oil.

This oil was isolated and then boiled for 30 minutes during which time the temperature of the vapour above the oil rose to 200° C. On cooling the residue solidified. Recrystallisation of the solid from methanol yielded 2-(2-benzyl-5-benzoxazolyl)propionitrile which was shown to be pure by thin layer chromatography.

Similarly the following nitriles were prepared and characterised:
 (b) 2-[2-(4-chlorobenzyl)-5-benzoxazolyl]propionitrile
 (c) 2-[2-(4-chlorobenzyl)-5-benzoxazolyl]acetonitrile
 (d) 2-[2-(4-chlorobenzyl)-6-benzoxazolyl]acetonitrile
 (e) 2-[2-(4-chlorobenzyl)-6-benzoxazolyl]propionitrile
 (f) 2-[2-benzyl-6-benzoxazolyl]acetonitrile
 (g) 2-[2-(3,4-dichlorobenzyl)-5-benzoxazolyl]propionitrile
 (h) 2-[2-(4-fluorobenzyl)-5-benzoxazolyl]propionitrile

EXAMPLE 11

Example 1(a) was repeated with the exception that:
 (a) phenylacetic acid.
 (b) phenylacetic anhydride,
 (c) phenyl acetamide, and
 (d) benzyl hydrazone,
were used instead of the phenyl acetyl chloride as the cyclising agent.

In each case, ethyl 2-(2-benzyl-5-benzoxazolyl) propionate was shown to have been formed by thin layer chromatography.

EXAMPLE 12 a. 4-chlorophenylisocyanate (3.1 g.) was slowly added to a stirred solution of 2-(3-amino-4-hydroxyphenyl propionitrile (3.3 g.) in xylene (3.5 ml.) at room temperature. When the addition was complete p-toluenesulphonic acid (250 mg.) was added, and the solution was heated under reflux using a Dean and Stark apparatus. On cooling the solution was washed with aqueous sodium bicarbonate solution and evaporated to dryness. The residue was recrystallised to give 2-[2-(4-chloroanilino)-5-benzoxazolyl]propionitrile as a creme solid which was characterised by n.m.r. spectroscopy.

b. Similarly, there was prepared:
 2-[2-anilino-5-benzoxazolyl]propionitrile

In the following Examples of pharmaceutical compositions of the present invention, the term "medicament" is used to indicate the compound 2-(2-benzyl-5-benzoxazolyl) propionic acid. That compound may of course by replaced by any other active compound of

15 formula I and the amount of medicament may be increased or decreased depending on the degree of activity of the medicament used.

EXAMPLE 13

Tablets each containing 100 mg. of medicament are made as follows:

| | |
|---|---|
| Medicament | 100 mg |
| Potato starch | 38 mg |
| Lactose | 25 mg |
| Ethyl cellulose | 2 mg |
| (as 20% solution in industrial alcohol) | |
| Alginic acid | 7 mg |
| Magnesium stearate | 1 mg |
| Talc | 2 mg |
| Total | 175 mg |

The medicament, starch and lactose are passed through a No. 44 mesh B.S.S. sieve and mixed thoroughly. The solution of ethyl cellulose is mixed with the resultant powders wich are then passed through a No. 12 mesh B.S.S. sieve. The granules produced are dried at 50°–60° C. and then passed through a No. 16 mesh B.S.S. sieve. the alginic acid, magnesium stearate and talc, previously passed through a No. 50 mesh B.S.S. sieve, are added to the granules, mixed and compressed in a tabletting machine to yield tablets each weighing 175 mg.

EXAMPLE 14

Capsules each containing 200 mg. of medicament are made as follows:

| | |
|---|---|
| Medicament | 200 mg |
| Lactose | 48 mg |
| Magnesium Stearate | 2 mg |

Th medicament, lactose and magnesium stearate are passed through a No. 44 mesh B.S.S. sieve and filled into hard gelatine capsules in 250 mg. quantities.

EXAMPLE 15

Injection solutions each containing 100 mg. of medicament per 5 ml solution are made as follows:

| | |
|---|---|
| Medicament | 100 mg |
| Sodium hydroxide (10% solution) | q.s. |
| Water for Injection | to 5 ml |

The medicament is suspended on the water and the sodium hydroxide solution added drop by drop with stirring until the medicament is in solution. The pH of the solution is adjusted to between 8.0 and 8.5, the solution is sterilised by filtration through a bacteria-proof filter and filled into previously sterilised glass ampoules which are then hermetically sealed under aspectic conditions.

EXAMPLE 16

Suppositories each containing 250 mg. of medicament are made as follows:

| | |
|---|---|
| Medicament | 250 mg. |
| Theobroma Oil | to 2000 mg. |

The medicament is passed through a No. 60 mesh B.S.S. sieve and suspended in the theobroma oil previously melted using the minimum of heat necessary. The mixture is then poured into a suppository mould of nominal 2 g. capacity and allowed to cool.

We claim:
1. A compound of the formula:

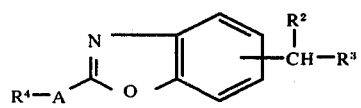

where the group

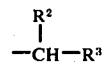

is in the 5- or 6- position of the benzoxazole nucleus, A is —CH$_2$—, —CO—,

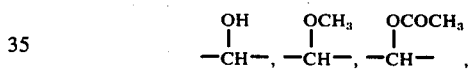

—NH— or —NCH$_3$—, R$^4$ is a phenyl group optionally substituted by one or two groups selected from halogen, trifluoromethyl, methyl, or methoxy, R$^2$ is hydrogen or methyl, and R$^3$ is the group COOR$^5$ wherein R$^5$ is C$_{1-4}$ alkyl or the group COOH or an alkali or alkaline earth metal, aluminum, or ammonium salt thereof.

2. A compound as claimed in claim 1, where A represents —CH$_2$—.

3. A compound as claimed in claim 1 which is 2-[2-benzyl-5-benzoxazolyl]propionic acid.

4. A pharmaceutical formulation comprising a chemotherapeutically effective amount of a pharmaceutically active compound of formula (I) as defined in claim 1 in association with at least one pharmaceutically acceptable carrier therefor.

5. A pharmaceutical formulation according to claim 4 wherein the compound of formula (I) is a compound in which A represents —CH$_2$—.

6. A method of treating a human suffering from arthritis which comprises the administration of a chemotherapeutically effective amount of an active compound of formula (I) as defined in claim 1.

* * * * *